United States Patent
Zhou et al.

(10) Patent No.: US 9,498,139 B2
(45) Date of Patent: Nov. 22, 2016

(54) BACKGROUND SUPPRESSION BY TIME DEPENDENT FLIP ANGLE OF SATURATION PULSES

(71) Applicant: TOSHIBA MEDICAL SYSTEMS CORPORATION, Tochigi (JP)

(72) Inventors: Xiangzhi Zhou, Vernon Hills, IL (US); Mitsue Miyazaki, Des Plaines, IL (US)

(73) Assignee: TOSHIBA MEDICAL SYSTEMS CORPORATION, Otawara-Shi, Tochigi-Ken (JP)

( * ) Notice: Subject to any disclaimer, the term of this patent is extended or adjusted under 35 U.S.C. 154(b) by 199 days.

(21) Appl. No.: 14/171,225

(22) Filed: Feb. 3, 2014

(65) Prior Publication Data

US 2015/0216428 A1 Aug. 6, 2015

(51) Int. Cl.
| | |
|---|---|
| *A61B 5/026* | (2006.01) |
| *A61B 5/00* | (2006.01) |
| *G01R 33/48* | (2006.01) |
| *G01R 33/483* | (2006.01) |
| *G01R 33/56* | (2006.01) |
| *G01R 33/561* | (2006.01) |
| *G01R 33/563* | (2006.01) |

(52) U.S. Cl.
CPC ........... *A61B 5/0263* (2013.01); *A61B 5/7292* (2013.01); *G01R 33/48* (2013.01); *G01R 33/4818* (2013.01); *G01R 33/4838* (2013.01); *A61B 5/0037* (2013.01); *G01R 33/5602* (2013.01); *G01R 33/5607* (2013.01); *G01R 33/5614* (2013.01); *G01R 33/5635* (2013.01)

(58) Field of Classification Search
CPC ..... A61B 5/055; A61B 5/026; A61B 5/0263
See application file for complete search history.

(56) References Cited

U.S. PATENT DOCUMENTS

| | | | | |
|---|---|---|---|---|
| 6,320,377 | B1 * | 11/2001 | Miyazaki | A61B 5/055 324/306 |
| 2011/0137146 | A1 | 6/2011 | Edelman | |
| 2012/0293172 | A1 * | 11/2012 | Wheaton | G01R 33/5635 324/309 |

OTHER PUBLICATIONS

Edelman et al., "Quiescent-Interval Single-Shot Unenhanced Magnetic Resonance Angiography of Peripheral Vascular Disease; Technical Considerations and Clinical Feasibility" *Magn Reson Med.* Apr. 2010; 63(4); 951-958. doi; 10.1002/mrm.22287.
Hodnett et al., Evaluation of Peripheral Arterial Disease with Nonenhanced Quiescent-Interval Single-Shot MR Angiography[1] Radiology: vol. 260: No. 1—Jul. 2011 radiology.rsna.org; pp. 282-293.

* cited by examiner

*Primary Examiner* — Peter Luong
(74) *Attorney, Agent, or Firm* — Nixon & Vanderhye P.C.

(57) ABSTRACT

A magnetic resonance imaging (MRI) system, method and/or computer readable storage medium is configured to effect QISS (quiescent interval single shot) MR imaging (e.g., MR angiography or MRA) where an optimized flip angle for one or more initial saturation pulses minimizes background signal from tissue and/or venous blood. Upon expiration of first configurable time interval from a start of a scan interval, at least one saturation pulse having a flip angle greater than ninety degrees is applied so that longitudinal magnetization of background tissue and venous blood in the selected area is approximately at a null value at the beginning of a readout time (occurring upon expiry of a second time interval) and/or when a lowest frequency of k-space data is acquired for the selected area.

20 Claims, 11 Drawing Sheets

BACKGROUND SUPPRESSION BY TIME DEPENDENT FLIP ANGLE OF SATURATION PULSES

FIELD

The subject matter below relates generally to magnetic resonance imaging (MRI), and more particularly to systems, methods, and computer readable storage medium for reducing background signal in MRA (magnetic resonance angiography) images.

DETAILED DESCRIPTION

Figure 1:
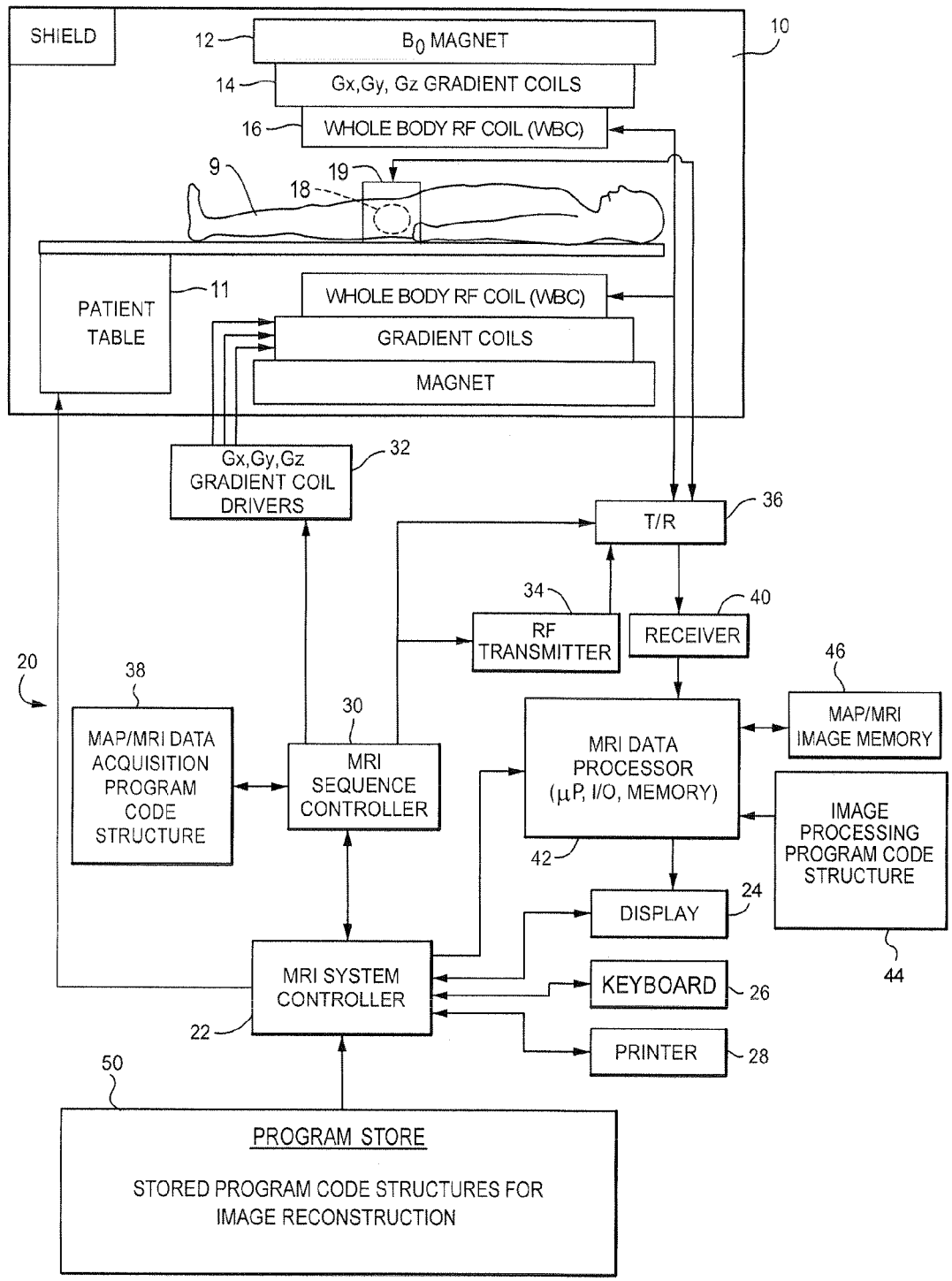
FIG. 1 is a high-level schematic block diagram of an MRI system, in accordance with one or more embodiments.

The MRI system shown in FIG. 1 includes a gantry 10 (shown in schematic cross-section) and various related system components 20 interfaced therewith. At least the gantry 10 is typically located in a shielded room. The MRI system geometry depicted in FIG. 1 includes a substantially coaxial cylindrical arrangement of the static field $B_0$ magnet 12, a Gx, Gy and Gz gradient coil set 14 and a large whole body radio frequency (RF) coil (WBC) assembly 16. Along the horizontal axis of this cylindrical array of elements is an imaging volume 18 shown as substantially encompassing a portion of the body of patient 9 supported by a patient table 11. A smaller array RF coil (AC) 19 might be coupled to a portion of the patient. The part of patient 9 that is subject to scanning using RF coil 19 is referred to herein, for example, as "scanned object" or "object" in imaging volume 18. As those in the art will appreciate, compared to the WBC (whole body coil), relatively small coils and/or arrays such as surface coils or the like are often customized for particular body parts (e.g., arms, shoulders, elbows, wrists, knees, legs, chest, spine, etc.). Such smaller RF coils are herein referred to as array coils (AC) or phased array coils (PAC). These may include at least one coil configured to transmit RF signals into the imaging volume and one or more receiver coils configured to receive RF signals from an object, such as the part of the patient body in the example above, in the imaging volume.

An MRI system controller 22 has input/output ports connected to a display 24, keyboard 26 and printer 28. As will be appreciated, the display 24 may be of the touchscreen variety so that it provides control inputs as well.

The MRI system controller 22 interfaces with MRI sequence controller 30 which, in turn, controls the Gx, Gy and Gz gradient coil drivers 32, as well as the RF transmitter 34 and the transmit/receive switch 36 (if the same RF coil is used for both transmission and reception). The MRI sequence controller 30 includes suitable program code structure 38 for implementing MRI imaging (also known as nuclear magnetic resonance, or NMR, imaging) techniques. The MRI imaging techniques may include, for example, parallel imaging and/or other imaging sequences.

The MRI system 20 includes an RF receiver 40 providing input to data processor 42 so as to create processed image data, which is sent to display 24. The MRI data processor 42 is also configured for access to system configuration parameters 46 and MRI image reconstruction program code structures 44 and 50. MRI image reconstruction program code structures 44 and 50 may, in addition to control logic for reconstructing MRI images, also include control logic to obtain MR data from RF coils 16 and/or 19. The MRI data processor 42 also operates to execute methods, such as, method 900 shown in FIG. 9 or parts thereof to achieve improved background suppression in MRI images.

Although shown in FIG. 1 as being located away from the RF coils 16 and 19, in some embodiments, any of RF transmitter 34, transmit/receive switch 36, and RF receiver 40 may be located in close proximity to, or on a surface of, either or both RF coils 16 and 19.

Also illustrated in FIG. 1 is a generalized depiction of an MRI system program store 50 where stored program code structures (e.g., for image reconstruction, for defining graphical user interfaces and accepting operator inputs to same, etc.) are stored in non-transitory computer-readable storage media accessible to the various data processing components of the MRI system. As those in the art will appreciate, the program store 50 may be segmented and directly connected, at least in part, to different ones of the system 20 processing computers having most immediate need for such stored program code structures in their normal operation (i.e., rather than being commonly stored and connected directly to the MRI system controller 22).

Indeed, as those in the art will appreciate, the FIG. 1 depiction is a very high-level simplified diagram of a typical MRI system with some modifications so as to practice exemplary embodiments described hereinbelow. The system components can be divided into different logical collections of "boxes" and typically comprise numerous digital signal processors (DSP), microprocessors and special purpose processing circuits (e.g., for fast A/D conversions, fast Fourier transforming, array processing, etc.). Each of those processors is typically a clocked "state machine" wherein the physical data processing circuits progress from one physical state to another upon the occurrence of each clock cycle (or predetermined number of clock cycles).

Not only does the physical state of processing circuits (e.g., CPUs, registers, buffers, arithmetic units, etc.) progressively change from one clock cycle to another during the course of operation, the physical state of associated data storage media (e.g., bit storage sites in magnetic storage media) is transformed from one state to another during operation of such a system. For example, at the conclusion of an image reconstruction process and/or sometimes a coil sensitivity map generation process, an array of computer-readable accessible data value storage sites in physical storage media will be transformed from some prior state (e.g., all uniform "zero" values or all "one" values) to a new state wherein the physical states at the physical sites of such an array vary between minimum and maximum values to represent real world physical events and conditions (e.g., the internal physical structures of a patient over an imaging volume space). As those in the art will appreciate, such arrays of stored data values represent and also constitute a physical structure—as does a particular structure of computer control program codes that, when sequentially loaded into instruction registers and executed by one or more CPUs of the MRI system 20, causes a particular sequence of operational states to occur and be transitioned through within the MRI system.

Example embodiments described below provide for using optimized flip angle saturation pulses to achieve improved background suppression in MRI images. In particular, exemplary embodiments may improve background suppression for tissue and venous blood in MRA images such as that obtained in peripheral vascular disease. Embodiments, including those which utilize double background saturation and some that apply a single saturation pulse for both tissue and blood, may yield improved background suppression compared to conventional approaches.

Example embodiments described herein may be applicable for MR imaging of any part of a patient. Some example embodiments are directed to MR imaging of calf, knee, iliac, regions. During the scanning process, with the patient located in the MRI gantry, one or more RF coils, such as whole body coil 16 and/or array coil 19, may transmit RF pulses to selected parts of the patient in order to excite nuclear magnetic resonance (NMR) spins in particular parts of the patient's body. For example, array coil 19, which is placed in the example at an area of the patient's body (e.g., knee area), may be used to excite nuclear spins specifically in that area. Subsequently, MR signals (e.g., echo signals) which are generated as a result of the earlier excitation are received by one or more RF receive coils. The transmitting of the RF pulses and the receiving of the MR signals may be done using the same RF coil (e.g., RF coil 19 configured for both transmit RF excitation pulses and receive corresponding MR signals) or by different RF coils (e.g., WBC 16 is configured to transmit RF pulses and RF coil 19 is configured to receive corresponding MR signals). In order to generate MRI images that are used for diagnostic or other purposes, data corresponding to the received MR signals must be communicated to a control system, such as a processing system including MRI data processor 42, for processing.

Quiescent inflow single-shot (QISS) non-contrast MRA technique is an emerging non-contrast MRA technique for peripheral MRA imaging. QISS has been found useful in diagnosing diseases such as peripheral vascular disease (PVD). QISS acquires data using a modified electrocardiographic (ECG)-triggered, fat suppressed, two-dimensional, balanced steady-state, free precession pulse sequence incorporating slice-selective saturation and a quiescent interval for maximal enhancement of inflowing blood.

Figure 2:
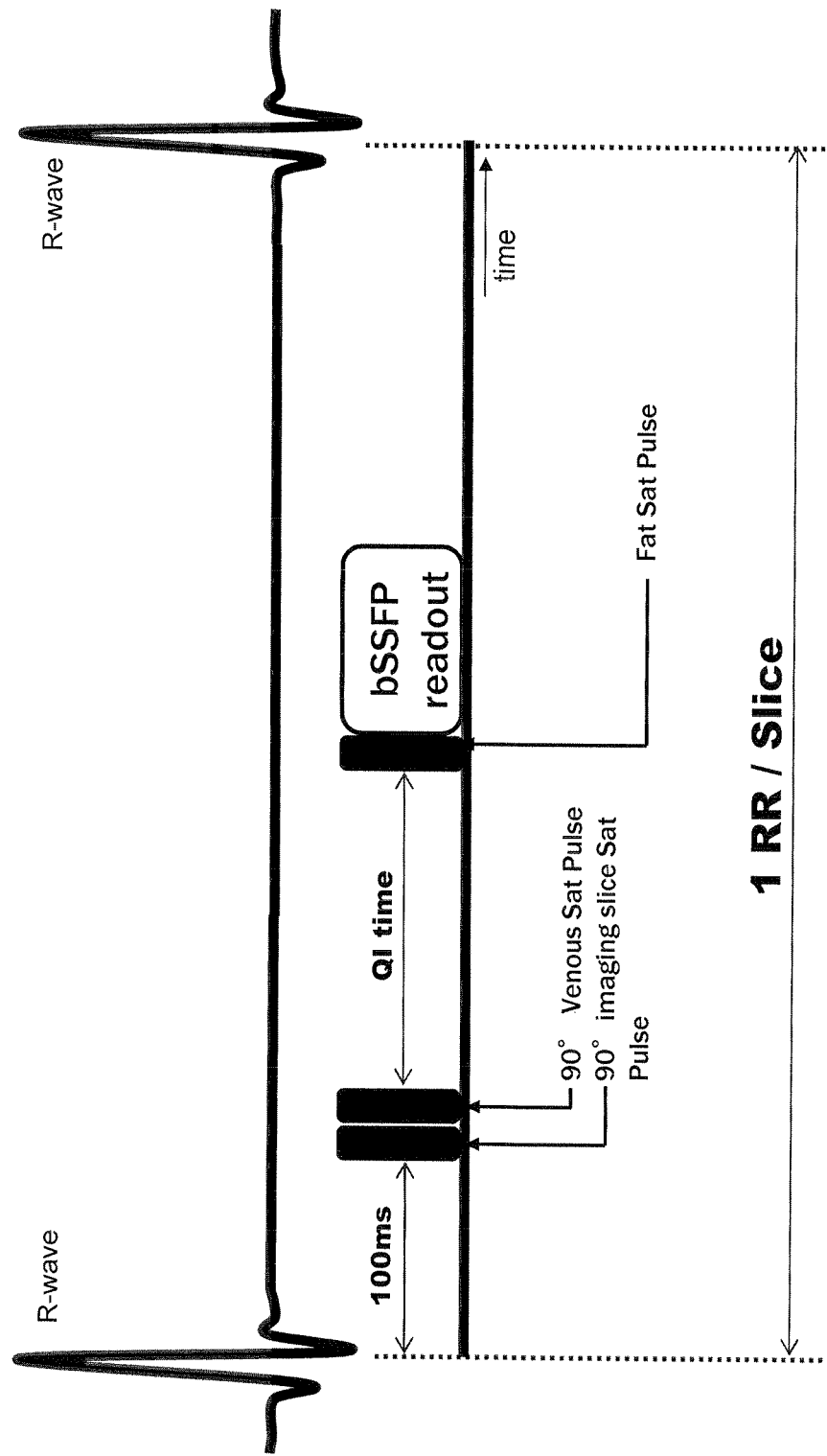
FIG. 2 illustrates a conventional quiescent-interval single shot (QISS) pulse sequence.

QISS is a 2D multiple slice imaging sequence that acquires one axial slice per heart beat, typically using 2D Balanced Steady-State Free Precession (bSSFP) readout. The QISS sequence is played in the following manner: about 100 ms after an R-wave, a selective 90° saturation pulse is generated to suppress background tissue signal in the imaged slice; and a 90° "walking" saturation pulse is generated to suppress incoming venous blood. A predetermined time interval follows after the two saturation pulses in order that the imaged area has fresh blood inflow of arterial blood and arrival at the more quiescent diastolic phase of the R-R cardiac cycle. This time interval is referred to as the quiescent interval (QI). After the QI time, a fat saturation pulse is generated to suppress the fat signal. Thereafter, a 2D bSSFP readout follows for data acquisition. FIG. 2 illustrates a conventional QISS pulse sequence.

Figure 3:
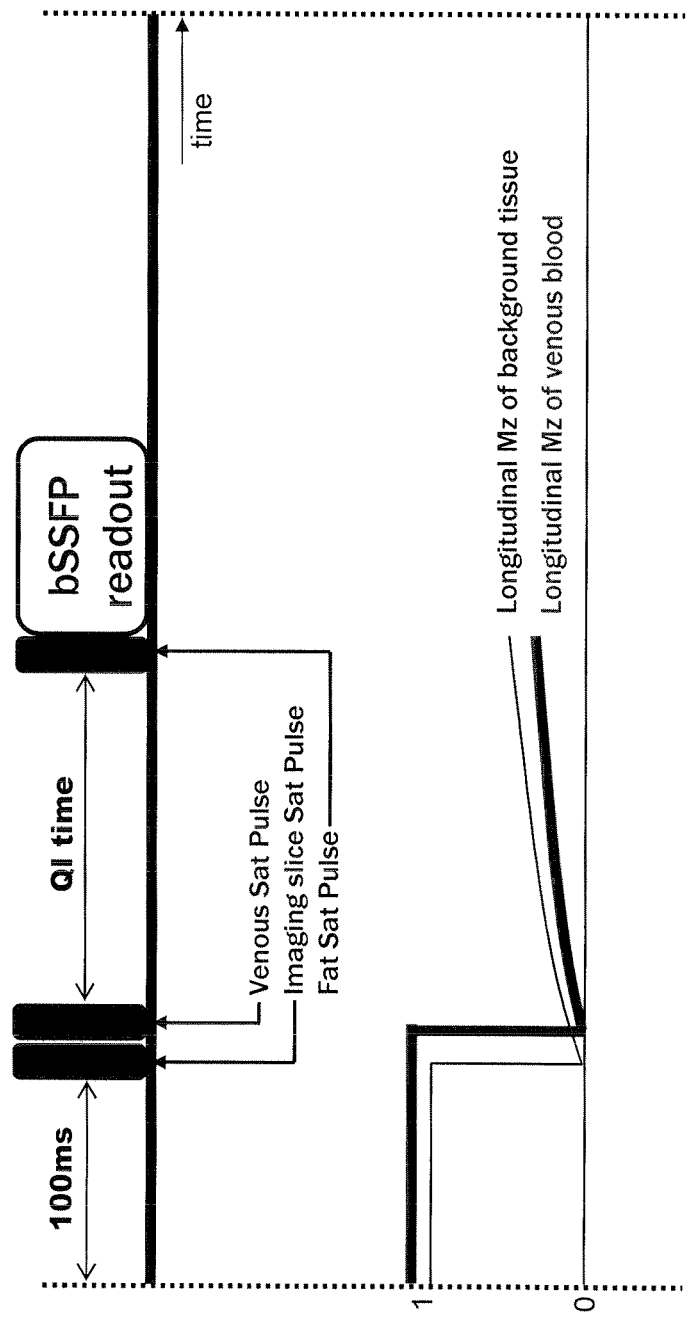
FIG. 3 illustrates longitudinal magnetizations of background and venous blood associated with the pulse sequence shown in FIG. 2.

The initial two saturation pulses in QISS are played to suppress background tissue signal and venous blood signal. However, the background tissue signal in the imaging slice and the venous blood signal, as they are used in QISS, partially recover before the start of data acquisition due to the QI time intervening between the generation of the saturation pulses and the data acquisition readout. FIG. 3 illustrates typical longitudinal NMR magnetization curves for background tissue and venous blood during a conventional QISS pulse sequence. The partial recovery of the background tissue signal and the venous blood signal prior to data acquisition leads to some degree of non-suppressed background and vein signals, and this may affect the diagnostic value of the arterial blood vessel in the QISS images.

Moreover, the initial two saturation pulses may result in a higher than desirable specific absorption rate (SAR) for the patient, and/or higher induced eddy currents due to the increased rate of change in time varying gradient fields (dB/dt), especially for thin imaging slices. Further, the inflow effect may not be optimized at different scanning stations of the human body (e.g., flow dependency at upper and lower body scanning stations). Conventional QISS may also be susceptible to artifacts due to use of the bSSFP sequence because bSSFP is more sensitive to field inhomogeneities than some other data acquisition sequences.

Figure 4:
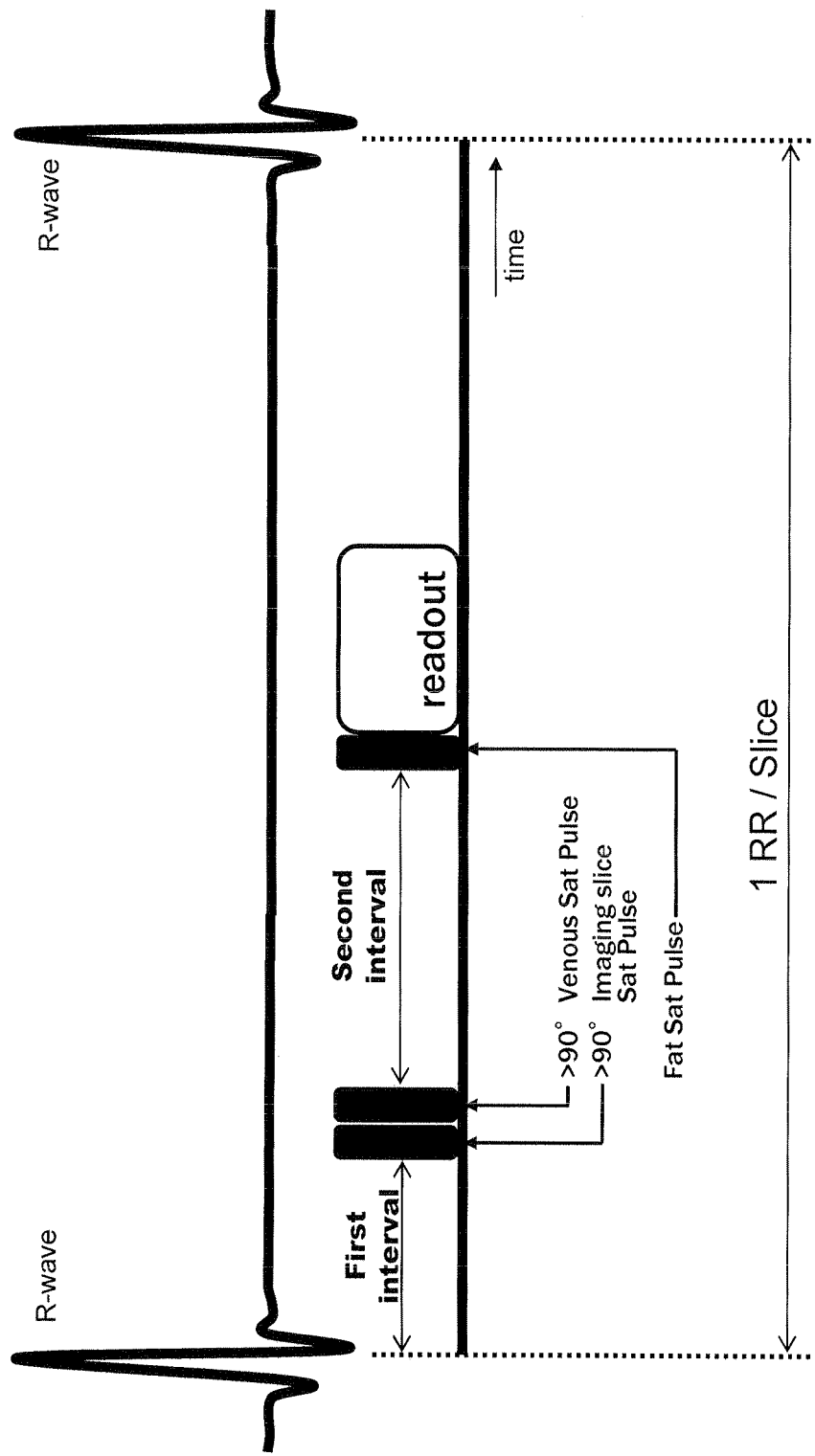
FIG. 4 illustrates an example pulse sequence with optimized saturation RF pulse flip angles for magnetic resonance angiography (MRA), in accordance with one or more embodiments.

FIG. 4 illustrates a pulse sequence for improved suppression of signals generated by background substance, such as, for example, venous blood and background tissue, in accordance with one or more embodiments. The sequence shown in FIG. 4 may be repeated for each scan interval. A single slice scan interval is, according to an embodiment, the time period between two adjacent R-waves. The sequence shown in FIG. 4 is repeated for each successive slice (the "walking" venous blood saturation pulse being spatially repositioned for each successive slice), as MR images of multiple axial slices of an area of interest (region of interest or "ROI") of the object are acquired.

After a configurable delay interval from the start of a scan interval, an optimized flip angle imaging slice background saturation RF pulse and an optimized flip angle venous blood saturation RF pulse are generated. The two pulses may be generated in quick succession, and may occur in any order.

A default value for the configurable initial delay interval from the start of the scan interval can be set at 100 ms. In embodiments, the configurable interval is set at values representing the estimated time for the imaged region to reach a systolic state after the R-wave.

The optimized flip angle for each RF saturation pulse may be separately determined. The flip angle is determined based upon a relevant known T1 recovery curve (e.g., T1 recovery curve for tissue, T1 recovery curve for blood, etc.) and the known time required for the object to reach a more quiescent state (e.g., diastolic) before obtaining the MRI data readout.

An image of a slice is preferably acquired in each imaging cycle. The optimized flip angle imaging slice background saturation pulse may be generated in the slice being imaged, and the optimized flip angle venous blood saturation pulse is preferably generated in a spatially walking saturation slab such that venous blood in the walking saturation slab arrives in the imaging slice after the optimized flip angle venous blood saturation pulse has been applied.

After the initial two saturation pulses are generated, a second configurable time QI interval is allowed to expire. The second configurable time interval is set so that fresh arterial blood that is not saturated is allowed to flow into the imaged area. During this time interval, the saturated venous blood also flows into the imaging area.

Upon the expiration of the second configurable time period, a fat saturation pulse is generated. Subsequent to the fat saturation pulse, MR data acquisition is commenced.

Figure 5:
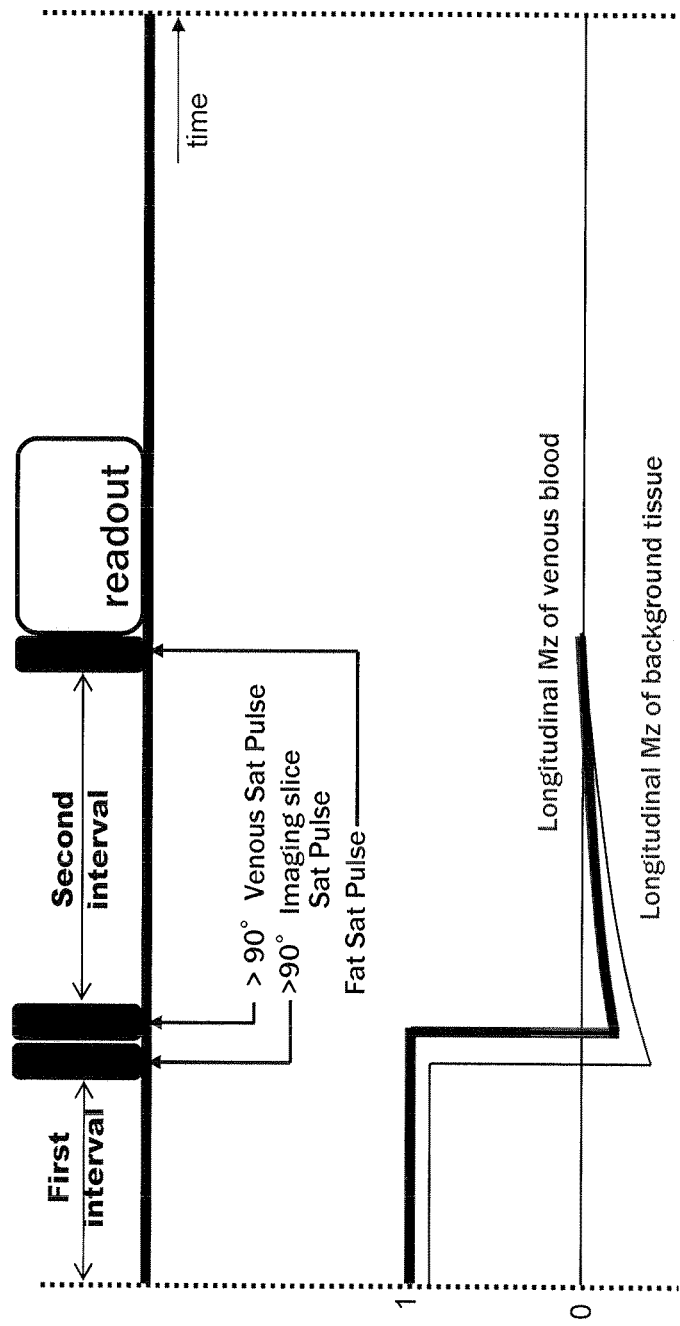
FIG. 5 illustrates the longitudinal magnetization associated with the pulse sequence shown in FIG. 4, in accordance with one or more embodiments.

FIG. 5 illustrates background tissue and venous blood longitudinal NMR magnetizations associated with embodiments. Upon generation of the saturation pulse, the longitudinal magnetization is purposefully made initially lower than 0 (e.g., between 0 and −1). This is in contrast to conventional QISS techniques in which the 90° saturation pulses initially produce longitudinal magnetizations of approximately 0.

The TI relaxation time recoveries of the longitudinal magnetizations are therefore now begun from this initial value. In embodiments, the initial longitudinal magnetizations are controlled by the flip angle of the respectfully associated RF saturation pulses. The flip angle is determined such that, given the known T1 recovery rates for background tissue and venous blood, by the time data acquisition is commenced (e.g., typically the time when a central k-space line of raw data is acquired), the longitudinal magnetizations do not recover to a value substantially greater than 0, but, instead, arrive at substantially zero magnetization.

Figure 6:
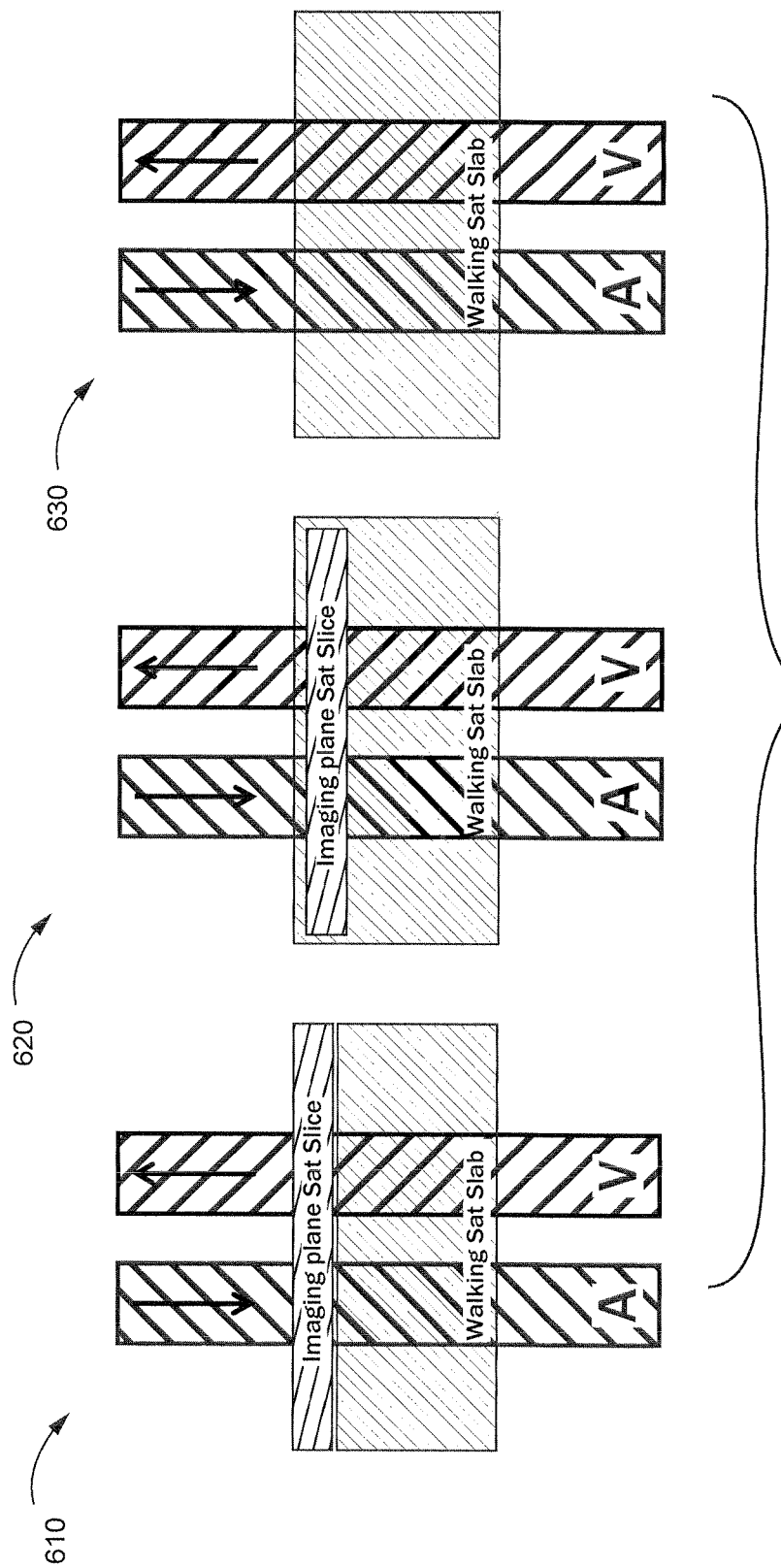
FIG. 6 illustrates techniques for selectively applying optimized flip angle pulses in accordance with some embodiments.

FIG. 6 illustrates techniques for applying optimized flip angle pulses in accordance with some embodiments. In the embodiment illustrated in diagram 610, the background tissue saturation pulse with an optimized flip angle is applied to the imaging slice, and the venous blood saturation pulse is applied to a separate area referred to as a walking saturation slab.

Note that, as shown in FIG. 6, venous blood V flows from the peripheries of the body upward in the direction of the heart. Arterial blood A flows in the opposite direction. Of course if the imaged area is saturated above the heart, the directions of arterial and venous blood flows would be reversed.

The size of the walking saturation slab is determined such that saturated venous blood either arrives in the imaged area ROI or is already in the imaged area ROI at the time of data acquisition.

The coverage of the walking saturation pulse can be extended to suppress both background signal and venous blood signal simultaneously. The imaging plane saturation pulse can be played together with the extended walking saturation pulse for double BGS (background suppression) or can be removed. The flip angle of this walking saturation pulse should be optimized so that the background signal is zero at the beginning of readout.

In the embodiment illustrated in diagram 620, the walking saturation slab size is determined so that it spatially overlaps the imaging saturation slice. The imaging saturation pulse is applied to the imaged area, and the venous blood saturation pulse is applied to the walking saturation slab. Thus, because both saturation pulses are applied to the imaged area, there is, in effect, double background tissue suppression in that area.

It should be noted that application of consecutive initial saturation pulses to the imaged slice (as shown in 620) does not result in doubling the effect on the longitudinal magnetization. When each saturation pulse is applied, it is immediately followed by spoiler gradients implemented in order to destroy transverse magnetization. Therefore, even when two or more saturation pulses are applied in a back-to-back manner, its effect on total magnetization is not additive.

In the embodiment illustrated in diagram 630, too, the walking saturation slab extends over the imaged slice. In the embodiment shown in 630, however, only one saturation pulse is applied. Thus, a single saturation pulse is, in this embodiment, applied to the venous blood saturation area and the imaged slice.

Figure 7:
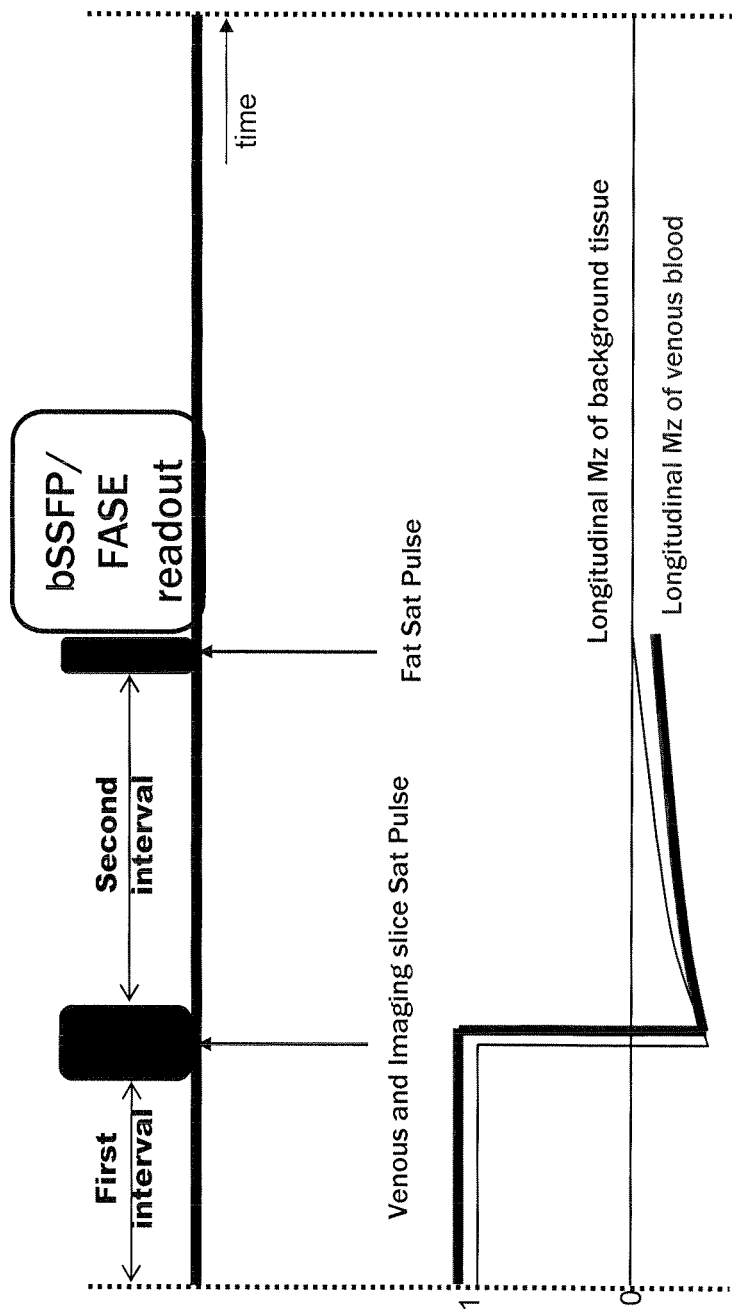
FIG. 7 illustrates another example sequence with optimized flip angles for MRA, in accordance with one or more embodiments.

FIG. 7 illustrates another example sequence with modified flip angles for MRA, in accordance with one or more embodiments. In the embodiment shown in FIG. 7, a single saturation pulse with optimized flip angle is applied (e.g., as spatially depicted in FIG. 6 at 630). The single saturation pulse is applied to the walking saturation slab which extends over the imaging slice as shown in 630.

Data acquisition may be performed using any of several techniques. For example, FASE (sometimes referred to as "single-shot FSE") readout is not so sensitive to field inhomogeneity. FASE read-out thus yields less susceptibility artifacts (e.g., banding artifacts) in background signals, especially at the iliac station where air and bone susceptibility effects are prominent. This is in contrast to bSSFP which is more sensitive to field inhomogeneities. The bSSFP sequence, however, yields a relatively higher signal to noise ratio for blood.

Figure 8:
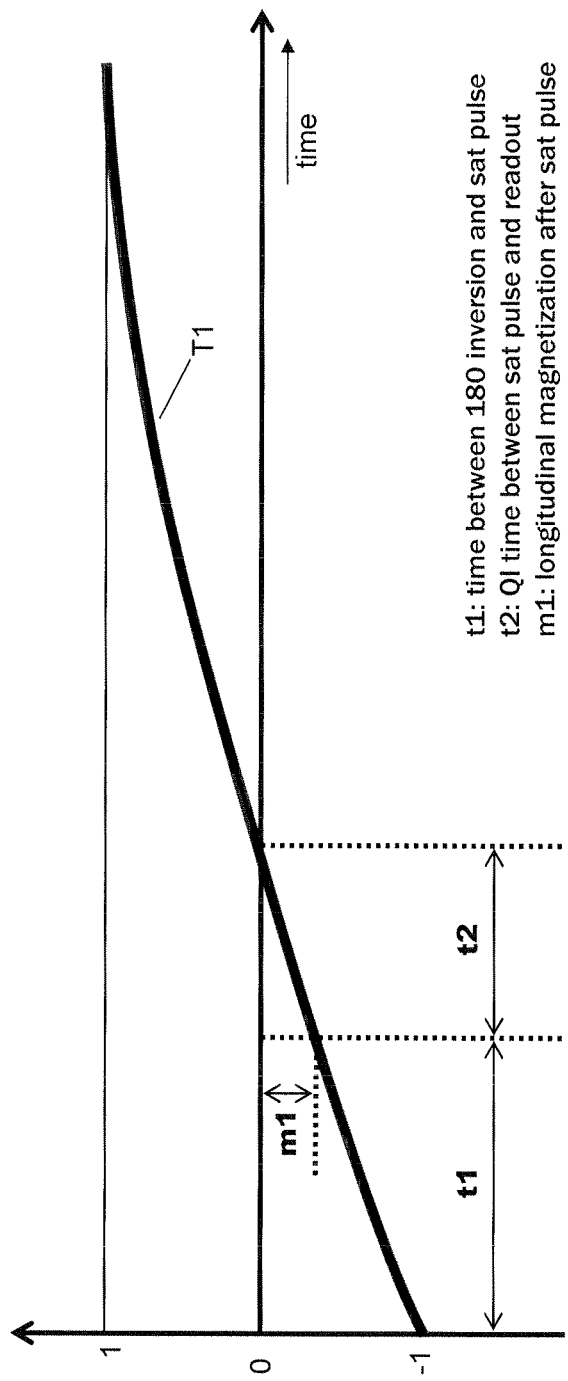
FIG. 8 illustrates a technique for determining flip angles, in accordance with one or more embodiments.

FIG. 8 illustrates a technique for determining optimized flip angles, in accordance with one or more embodiments.

The T1 spin lattice relaxation curves are known for background tissue and blood. The illustrated T1 curve may, for example, show magnetization recovery between −1 and 1, such as when recovering after a 180° inversion pulse. Based upon the requirement that longitudinal magnetization preferably should be at zero when the MRI acquisition sequence is begun or when a central line of k-space data (e.g., lowest frequency k-space data) is acquired, QI (which is denoted t2 in FIG. 8) is preset, usually to value such as 200 ms. From the above, t1 can then also be determined as it represents the time interval from the start of the scan interval (e.g., an R-wave) to the time when the at least one initial saturation pulse is generated.

Based upon t1 and T1, m1 (which represents longitudinal magnetization immediately after the initial saturation pulse(s) is (are) applied) is determinable.

The optimum flip angle can then be determined based upon the determined m1 value.

The set of equations 810 illustrate one technique for determining an optimized flip angle according to some embodiments.

Figure 9:
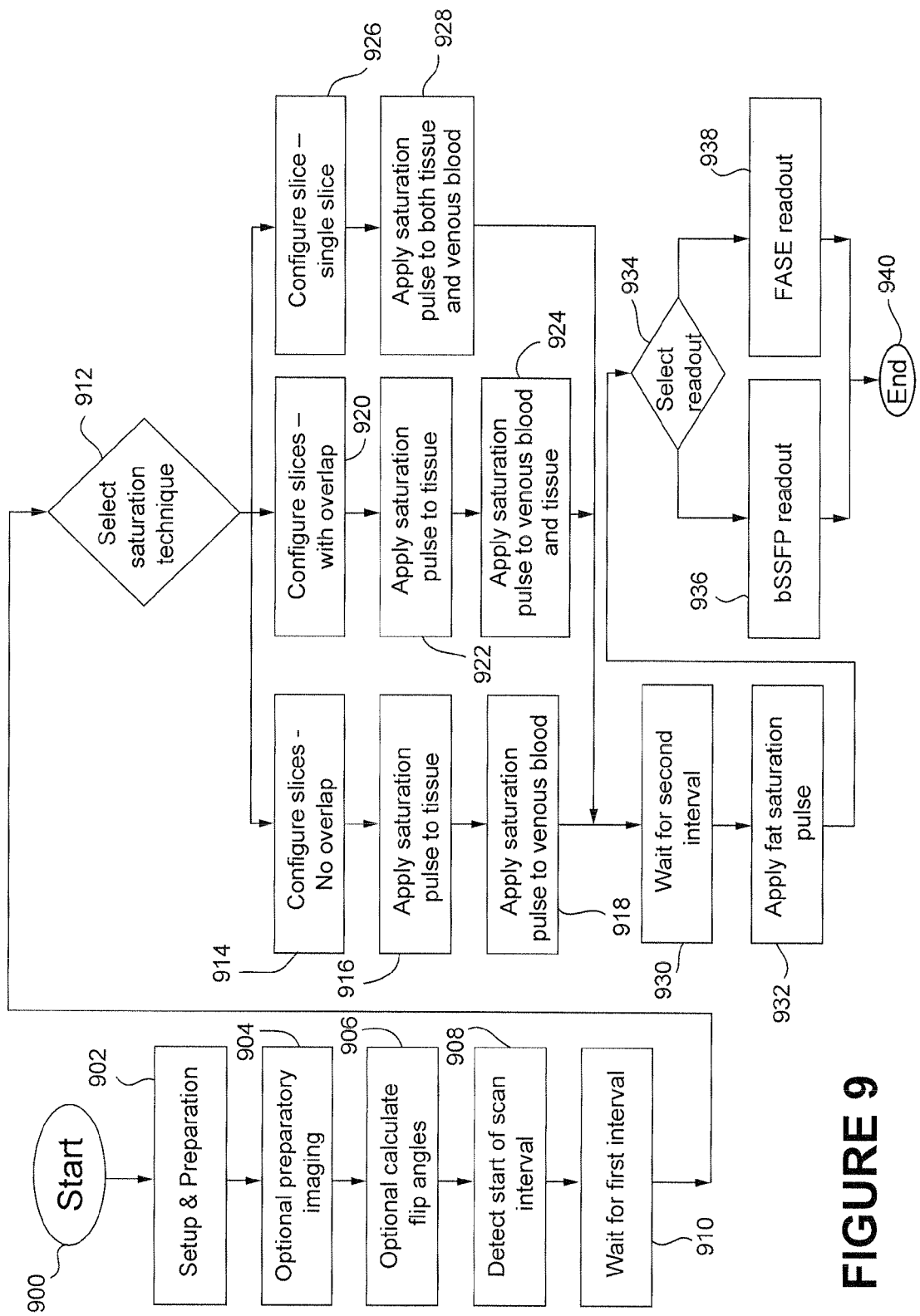
FIG. 9 illustrates a flowchart of a method of background suppression using optimized flip angles, in accordance with one or more embodiments.

FIG. 9 illustrates a flowchart for a method 900 that achieves improved background suppression with optimized flip angles, in accordance with one or more embodiments. Method 900 may be performed by operations 902-940 in the order shown, or in another order, and may include one or more additional operations, or exclude one or more operations 902-940.

At operation 902, the patient (e.g., object) is prepared and setup in the MRI machine for scanning.

At operation 904, optional preparatory scanning may be performed. For example, a preparatory scan may, for example, using cine imaging together with an electrocardiogram, identify the cardiac rhythm (e.g., interval between two R-waves of the ECG cycle) for the patient. The preparatory scan may, for example, enable determining t1+t2, and/or enable customizing the t1 and t2 values for each patient. An option may be to conduct cine-imaging to recognize, among other things, the occurrence of an R-wave, and/or the time for the patient (or the patient's region to be imaged) reach the diastolic stage. By identifying such parameters for a patient, the t1 and t2 values may be customized for each patient, for a more accurate flip angle for the initial saturation pulses that would result in substantially zero longitudinal magnetization when the readout begins and/or when the central line of k-space data is acquired. Customizing t1 and t2 according to a patient's heart rate, as discussed above, may be done manually or automatically. The detection of the scan interval may be manual and/or fully-automated.

At operation 906, the optimized flip angles are determined. Determining the optimized flip angles may be based upon dynamic calculations, or upon looking up previously calculated values, or a combination thereof.

According to one embodiment, the optimized flip angle for tissue background suppression and the optimized flip angle for venous blood background suppression are calculated based upon known parameters such as the known T1 curves, known or configured quiescent time intervals, and/or known time from start of a scan interval to data acquisition. A technique for calculating an optimized flip angle was described above in relation to FIG. 8.

According to another embodiment, the optimized flip angle values that have been previously calculated and stored are accessed in order to determine the flip angle to be used. The previously calculated values may be stored in a memory local to the MRI machine or at a network location accessed by a process executing on the MRI machine.

Besides better background tissue and venous blood signal suppression example embodiments improve protocol setting efficiency and reduce SAR and dB/dt, if only the extended walking saturation pulse is played to suppress both background tissue and venous signal. The inflow effect is maximized by optimizing the QI period.

At operation 908, a start of a scan interval is automatically detected. The start of the scan interval may be based upon detecting an R-wave.

After detection of the start of the scan interval, at operation 910, the method waits for a first configurable time interval. The first configurable time interval may be set for the time taken for the object ROI to reach a systolic state.

At operation 912, the optimized flip angle saturation pulse technique to be applied is selected (e.g., based upon prior operator inputs).

One of the techniques shown in FIG. 6 may be selected. The selection may be based, at least in part, upon the desired level of background suppression, SAR constraints of the object, and/or other such considerations.

In some embodiments, technique 610 may be selected. When technique 610 is selected, an image saturation slice and a walking saturation slice are determined at operation 914. Thereafter, at operation 916 the image saturation pulse with the optimized flip angle is applied to the image saturation slice. At operation 918, a venous blood suppression pulse is applied to the walking saturation slab area. The image saturation pulse and venous blood saturation pulse are applied to separate areas with no overlap.

If a high level of background suppression is desired, then the technique associated with 620 above may be selected at operation 912. As noted above 620 results in double background suppression in the imaging slice. When the technique associated with 620 above is selected, at operation 920, the size of the imaging slice and the size of the walking saturation slice are configured. The walking saturation slab is configured to fully overlap the imaging slice. After the slices are configured, at operation 922, the image saturation pulse with the optimized flip angle is applied to the image saturation slice. At operation 924, a venous blood suppression pulse is applied to the walking saturation slab area.

Under certain SAR constraints, two separate saturation pulses may not be desirable. Thus, in the event that SAR constraints are important the technique 630 may be selected for background suppression.

When technique 630 is selected, at operation 926, the walking saturation slab is configured to encompass the imaging saturation slice. At operation 928, a single saturation pulse is applied to the entire walking saturation slab. In this technique, separate pulses for venous blood and tissue are not applied.

After any of the three possible paths of execution from 912, after the one or more saturation pulses are applied, at operation 930, method 900 waits for a second configurable time interval. As also noted above, the wait for the second configurable time interval is referred to as a quiescent interval QI and may be configured so that the object ROI is estimated as returned to the diastolic state of a cardiac cycle.

In some embodiments, the second configurable time interval QI is set to a predetermined value. A default value may be 230 ms. In some embodiments, however, the second configurable time may be customized for each patient. For example, based upon the preparatory scan and the patient's cardiac cycle determined from the preparatory scan, the average systolic to diastolic time intervals for the ROI may be determined, which in turn can be used for determining the second configurable time interval. The second configurable time interval may also be customizable from one patient body in imaging station to another because the speed of blood flow may differ from one place in the body to another. Customizing the second configurable interval to the patient may allow for maximizing the inflow effect that depends on the interval QI. The second configurable time interval may be adjusted based upon the blood flow speed at the body station being imaged. For example, the QI for lower abdomen, thigh, and calf station are different: the faster the blood flow speed, the shorter the QI period. In a similar manner, some embodiments may use values customized for each patient for the first configurable time interval.

Upon expiration of the second configurable time interval, at operation 932, a conventional fat saturation pulse is generated. This pulse is for suppressing the fat signal just prior to data acquisition.

At operation 934, a readout technique is selected (e.g., based on previous operations set-up inputs).

In some embodiments, bSSFP readout is performed at operation 936.

In some other embodiments, FASE readout is performed at operation 938. FASE readout may be advantageous when field inhomogeneities are present. bSSFP generally yields a better signal to noise ratio.

After the MR data acquisition at operations 936 or 938, method 900 proceeds to operation 940 where image reconstruction (i.e., Fourier transformation of raw k-space data) can be performed using the acquired MR data.

Figure 10:
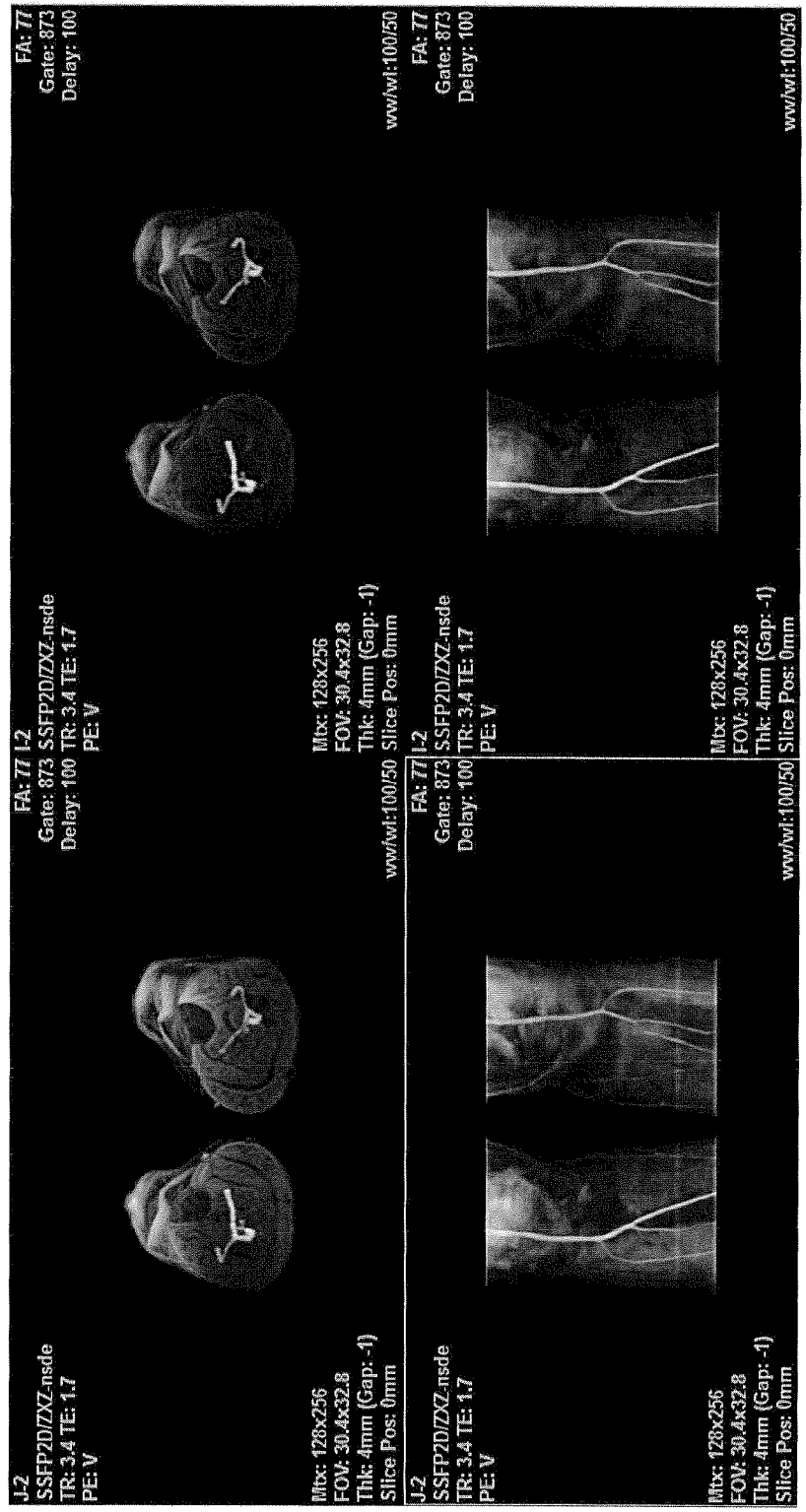
FIG. 10 shows a comparison of MRA images acquired according to conventional techniques and MRA images acquired with background suppression using optimized flip angles in accordance with one or more embodiments.

FIG. 10 shows a comparison of MRA images acquired according to conventional techniques and MRA images acquired with background suppression using optimized flip angles in accordance with one or more embodiments.

Specifically, in FIG. 10, the top row shows axial images and the bottom row shows coronal images. The left column illustrates images acquired using conventional QISS with 90° flip angles. The right column illustrates images acquired using one or more embodiments with optimized flip angles of imaging slice saturation pulse and walk saturation pulse. The MIP images on the right show better background suppression and venous signal suppression with optimized flip angle of imaging slice saturation pulse and walk saturation pulse.

Figure 11:
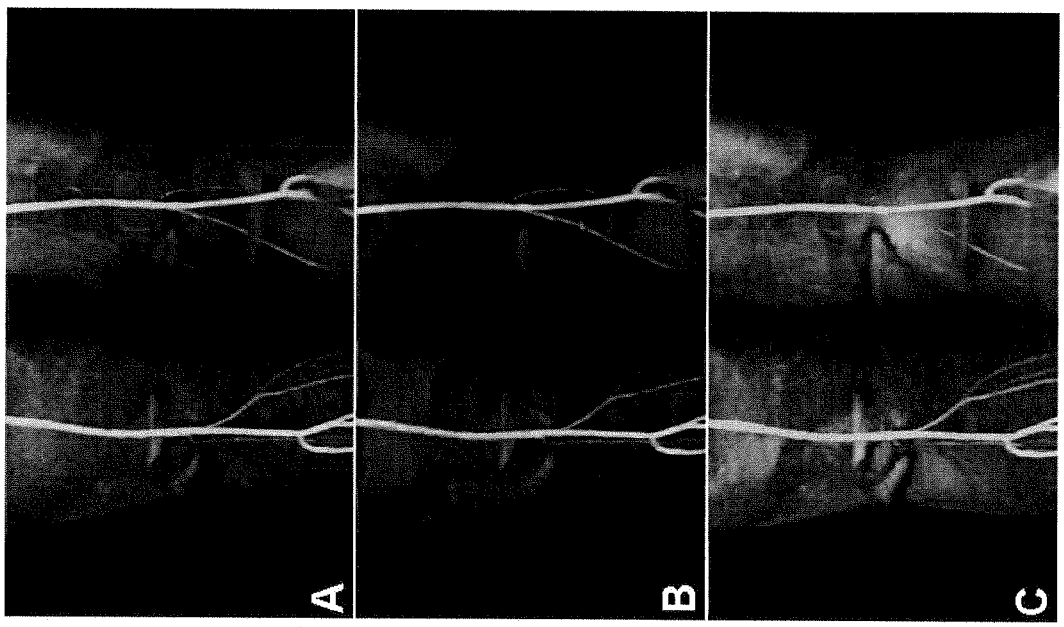
FIG. 11 shows a further comparison of MRA images acquired according to conventional techniques and according to one or more embodiments.

FIG. 11 shows a further comparison of MRA images acquired according to conventional techniques and according to one or more embodiments.

Coronal maximum intensity projection (MIP) images at the calf station of a healthy volunteer acquired by 3 different background saturation techniques described in relation to FIG. 6 are illustrated. The three background suppression techniques are: A, using the imaging slice saturation for single background suppression; B, extended walking saturation slab for double background suppression; and C extended walking saturation slab for background suppression without imaging slice saturation pulse. The three MIP images are windowed at the same level. The extended walking saturation slab B for double background suppression is seen to yield the clearest image with substantially less background signal.

The following is an example at 3 Tesla. Assume T1 for background tissue is 1400 MS, T1 for blood is 100 mg, and the QI time is 220 MS. According to the equations 810, the optimized flip angle of the imaging plane saturation pulse should be about 100° and the flip angle of the walking saturation pulse should be about 99°.

While certain embodiments have been described, these embodiments have been presented by way of example only and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A magnetic resonance imaging (MRI) system comprising:
   an MRI gantry including a static magnetic field coil, gradient magnetic field coils, at least one radio frequency (RF) coil configured to transmit RF nuclear excitation pulses into an imaging volume, and to receive nuclear magnetic resonance (NMR) RF signals from an object located in the imaging volume; and
   control circuits configured to control gradient magnetic fields generated by said gradient magnetic field coils, and to transmit/receive RF signals to and from said at least one RF coil, the control circuits being configured to perform operations comprising:
      generating, in a selected walking slab area of the object, upon expiration of a first time interval from a start of a scan interval, at least one RF saturation pulse having a flip angle greater than ninety degrees, the flip angle being configured so that longitudinal magnetization of background substance including venous blood flow in an area to be imaged is substantially nulled at a readout time occurring upon expiry of a second time interval, the selected walking slab area spatially overlapping the area to be imaged;
      generating, during said readout time, an MRI data acquisition sequence for the area to be imaged so as to generate MRI signals from non-saturated arterial blood flowing into the area to be imaged; and
      receiving said digital MRI signals from said at least one RF coil during the readout time and using the received MRI signals to reconstruct an MR image of arterial blood flow in the area to be imaged.

2. The MRI system according to claim 1, wherein the second time interval is configurable and dimensioned to cause said substantial nulling at a readout time for a central position of k-space.

3. The MRI system according to claim 1, wherein said at least one RF saturation pulse comprises both an imaging plane background saturation pulse and a venous blood suppression pulse, each having flip angles configured to substantially null respectively associated NMR magnetization signals at a readout time for a central position of k-space.

4. The MRI system according to claim 1, wherein the flip angle is based upon a predetermined T1 spin lattice relaxation curve and the second time interval which has been configured to maximize inflow of fresh arterial blood into the area to be imaged before said readout time.

5. The MRI system according to claim 4, wherein the first time interval is configurable and set to a time interval for reaching a systolic stage of the cardiac cycle in the area to be imaged, and wherein the second time interval is configurable and set to a time interval for reaching a diastolic state of the cardiac cycle in the area to be imaged.

6. The MRI system according to claim 4, wherein the second time interval is configurable and based at least in part upon blood flow speed in the selected area to be imaged.

7. MRI system according to claim 1, wherein the at least one RF saturation pulse comprises:
   an imaging slice RF saturation pulse in at least a portion of the selected area; and
   a venous saturation pulse in a walking saturation slab located in the selected area contiguous to or overlapped with said imaging slice.

8. The MRI system according to claim 1, wherein the MRI data acquisition sequence uses a 2D fast acquisition spin echo (FASE) technique.

9. A magnetic resonance imaging (MRI) method, comprising:
   generate, in a selected walking slab area of an object located in an MRI gantry, upon expiration of a first time interval from a start of a scan interval, at least one RF saturation pulse having a flip angle greater than ninety degrees, the flip angle being configured so that longitudinal magnetization of background substance including venous blood flow in an area to be imaged is substantially nulled at a readout time occurring upon expiry of a second time interval, the selected walking slab area spatially overlapping the area to be imaged;
   generate, during said readout time, an MRI data acquisition in the area to be imaged so as to generate MRI signals from non-saturated arterial blood flowing into the area to be imaged; and
   receive said digital MRI signals from said at least one RF coil during the readout time and use the received MRI signals to reconstruct an MR image of arterial blood flow in the area to be imaged.

10. The MRI method according to claim 9, wherein the second time interval is configurable and dimensioned to cause said substantial nulling at a readout time for a central position of k-space.

11. The MRI method according to claim 9, wherein said at least one RF saturation pulse comprises both an imaging plane background saturation pulse and a venous blood suppression pulse, each having flip angles configured to substantially null respectively associated NMR magnetization signals at the a readout time for a central position of k-space.

12. MRI method according to claim 9, wherein the flip angle is based upon a predetermined T1 spin lattice relaxation curve and the second time interval which has been configured to maximize in flow of fresh arterial blood into the area to be imaged before said readout time.

13. MRI method according to claim 12, wherein the first time interval is configurable and set to a time interval for reaching a systolic stage of the cardiac cycle in the area to be imaged, and wherein the second time interval is configurable and set to a time interval for reaching a diastolic state of the cardiac cycle in the area to be imaged.

14. The MRI method according to claim 13, wherein the second time interval is configurable and based at least in part upon blood flow speed in the selected area to be imaged.

15. The MRI method according to claim 9, wherein the at least one RF saturation pulse comprises:
   an imaging slice RF saturation pulse in the area to be imaged; and
   a venous saturation pulse in a walking saturation slab located in the selected area contiguous to or overlapped with said imaging slice.

16. The MRI method according to claim 9, wherein the MRI data acquisition sequence uses a 2D fast acquisition spin echo (FASE) technique.

17. A non-transitory computer readable storage medium having stored thereon instructions, that when executed by a processor of a magnetic resonance imaging (MRI) system, causes the MRI system to perform operations comprising:
   generating, in a selected walking slab area of the object, upon expiration of a first time interval from a start of a scan interval, at least one RF saturation pulse having a flip angle greater than ninety degrees, the flip angle being configured so that longitudinal magnetization of background substance including venous blood flow in an area to be imaged is substantially nulled at a readout time occurring upon expiry of a second time interval, the selected walking slab area spatially overlapping the area to be imaged;
   generating, during said readout time, an MRI data acquisition sequence for the area to be imaged so as to generate MRI signals from non-saturated arterial blood flowing into the area to be imaged; and
   receiving said MRI signals from said at least one RF coil during the readout time and using the received MRI signals to reconstruct an MR image of arterial blood flow in the area to be imaged.

18. The computer readable medium of claim 17, wherein said at least one RF saturation pulse comprises both an imaging plane background saturation pulse and a venous blood suppression pulse, each having flip angles configured to substantially null respectively associated NMR magnetization signals at the beginning of the readout time.

19. A magnetic resonance imaging (MRI) system comprising:
   an MRI gantry including a static magnetic field coil, gradient magnetic field coils, at least one radio frequency (RF) coil configured to transmit RF nuclear excitation pulses into an imaging volume, and to receive nuclear magnetic resonance (NMR) RF signals from an object located in the imaging volume; and
   control circuits configured to control gradient magnetic fields generated by said gradient magnetic field coils, and to transmit/receive RF signals to and from said at least one RF coil, the control circuits being configured to perform operations comprising:
   generating, in a selected walking slab area of the object, upon expiration of a time interval from a start of a scan interval, at least one RF saturation pulse having a flip angle greater than ninety degrees, the flip angle being configured so that longitudinal magnetization of background substance including venous blood flow in an area to be imaged is substantially nulled when a lowest frequency of k-space data is acquired for the selected area, the selected walking slab area spatially overlapping the area to be imaged;
   generating, during a readout time, an MRI data acquisition sequence for the area to be imaged so as to generate MRI signals from non-saturated arterial blood flowing into the area to be imaged; and
   receiving said MRI signals from said at least one RF coil during the readout time and using the received MRI signals to reconstruct an MR image of arterial blood flow in the area to be imaged.

20. The MRI system according to claim 19, wherein the lowest frequency of k-space data is acquired for the selected area at a beginning of the readout time occurring upon expiry of a second time interval from application of said at least one RF saturation pulse.

* * * * *